United States Patent [19]

Hill et al.

[11] Patent Number: 5,145,788
[45] Date of Patent: Sep. 8, 1992

[54] ASSAY

[75] Inventors: Martyn W. Hill, Essex; Dennis F. Sharman, Cambridge, both of Great Britain

[73] Assignee: CTS Biocides, Limited, Cambridge, England

[21] Appl. No.: 605,485

[22] Filed: Oct. 30, 1990

Related U.S. Application Data

[63] Continuation-in-part of PCT/GB89/00507

[30] Foreign Application Priority Data

May 17, 1988 [GB] United Kingdom ............... 8811617

[51] Int. Cl.$^5$ ........................................... G01N 21/75
[52] U.S. Cl. ................................... 436/106; 436/131; 436/132; 436/164; 436/175
[58] Field of Search ............... 436/131, 132, 164, 175, 436/106

[56] References Cited

FOREIGN PATENT DOCUMENTS 0254780  2/1988  European Pat. Off. .
2282411  6/1976  France .
0654898  3/1979  U.S.S.R. .
1286969  1/1987  U.S.S.R. .

OTHER PUBLICATIONS

N. De Kruijf et al., "Thin-Layer Chromatographic Procedure for the Identification of Preservatives in Cosmetic Products", Journal of Chromatography, 410 (1987), 395–411.

Primary Examiner—David L. Lacey
Assistant Examiner—David Redding
Attorney, Agent, or Firm—Oliff & Berridge

[57] ABSTRACT

A method for assaying Bronopol or Permachem, i.e. 2-bromo-2-nitro-1,3-propanediol or 2,2-dibromo-2-nitroethanol, or a derivative thereof in a sample, comprises adding to the sample a diazo compound which reacts with the compound under test to form a colored species, and determining the presence and, if desired, concentration of the species colorimetrically.

10 Claims, No Drawings

ASSAY

This is a continuation-in-part application of Ser. No. PCT/GB89/00507, filed May 11, 1989.

FIELD OF THE INVENTION

This invention relates to an assay for Bronopol (2-bromo-2-nitro-1,3-propanediol) Permachem N21 (2,2-dibromo-2-nitroethanol), and derivatives thereof. The invention relates also to kits which can be used in such an assay.

BACKGROUND OF THE INVENTION

Bronopol is a well-known compound, widely used in cutting fluids, in water-treatment and as a preservative in, for example, pharmaceuticals, cosmetics and toiletries. For water-treatment, and in particular for the control of Legionnaires' disease, it and also Permachem, could be added to cooling towers.

Although these known compounds are very valuable for the purposes for which they are used, the amount which is added is often uncontrolled and may in fact be far too great for the intended purpose. For example, Bronopol is stable, under normal conditions, and large excesses of the compound may be used in a way which is ultimately undesirable from an environmental or other viewpoint.

It is therefore desirable to quantify the amount of the compound which is used, so that the amount can be controlled more accurately for correlation with the intended purpose. It is known to assay Bronopol by HPLC or GLC (using the acetyl derivative and electron capture), but both these assays are undesirably long and complex.

SUMMARY OF THE INVENTION

A colorimetric assay for the given compounds has been devised, based on the discovery that a diazo compound will complex with them, to give a characteristic red or other colour, under certain conditions. Colorimetric analysis can then be conducted simply to determine the presence and, if desired, concentration of the coloured species.

DESCRIPTION OF THE INVENTION

The diazo compound (or any other suitable agent) must have the ability to react, perhaps by forming a complex, with the compound under test. For example, it appears that a derivative of bronopol, by hydrolysis, usually under alkaline conditions, is 2-bromo-2-nitroethanol. The diazo compound will therefore usually be capable of reacting or complexing with a compound of the formula $CH_2OH-CR_1R_2NO_2$ or $CH_2OH-CR-NO_2-CH_2OH$ (wherein R, $R_1$ and $R_2$ are each H or a substituent, e.g. a leaving group such as Br.

Preferred diazo compounds are derived from 4-nitroaniline or another aniline having a 2- or 4-electron-withdrawing substituent. Such diazo compounds appear to give the distinctive red colour which is preferred for the purposes of colorimetric analysis. Distinction lies in the fact that, under the conditions of the assay, other coloured species may be formed, e.g. owing to the presence of phenolic components in the sample to be assayed, but such coloured species will usually be, say, yellow and can be separated accordingly.

Many diazo compounds will give a colour, even if not a red colour, on reaction or complex-formation with bronopol or a derivative thereof. The colour may not be distinguishable from the colour produced under the conditions of the assay in consequence of the presence of other components in the sample; if the desired colour is not distinctive, an assay of the invention may be conducted by first removing such components. The desired colour which is formed may, if necessary or desired, be stabilised by using, say, a chlorinated phenol.

The desired colour may form in alkaline conditions. A preferred assay method in accordance with the invention comprises the sequential steps of (1) making the sample alkaline; (2) neutralising the alkaline sample; (3) adding the diazo compound and making the neutral sample alkaline; (4) adding a stabiliser for the colour; and (5) determining the presence and, if desired, concentration of coloured species. Undesirable components may first be removed, as described above.

In step (1), the addition of sodium carbonate or another salt of a weak acid makes the sample alkaline (e.g. pH 10). Under these conditions, Bronopol is probably converted to 2-bromo-2-nitroethanol.

Acetic acid or another weak acid is then added to neutralise (pH=7) the alkaline sample. The subsequent addition of the diazo compound and sodium carbonate or another salt of a weak acid gives a colour associated with the compound under test (at about pH 10) which can be read colorimetrically. A yellow colour indicates the presence of colour-giving components other than the compound under test, and these can be removed as desired.

Colorimetric analysis can be by any conventional means. For example, a colorimeter may be used for assay analysis. For more immediate results, the coloured sample may be compared with a chart of varying, calibrated colours.

The desired coloured species is, for example, a 1:1 complex. If excess diazo compound is added, the colour which is produced in the sample may fade with time. However, this is not a problem if the colour is determined shortly after causing the colour to be formed Nevertheless, a stabiliser for the colour is preferably added.

An assay kit which is suitable for use in a process according to the invention comprises three separate containers respectively containing an alkali, an acid and the diazo compound. As indicated above, the alkali may be sodium carbonate or another salt of a weak acid, while the acid is usually a weak acid such as acetic acid. The kit may also comprise a stabiliser in a separate container, or in stable admixture with one of the other components.

An advantage of the novel assay, especially in connection with the determination of Bronopol in water systems, is that many standard corrosion inhibitors do not interfere.

The following Examples illustrate the invention.

EXAMPLE 1

Sodium carbonate was added to an aqueous solution of Bronopol (10 µg/ml) to give a concentration of 0.1M $Na_2CO_3$. Fast Scarlet GG salt was then added to give a concentration of 1.3 mg/ml. The intensity of the resulting orange colour was measured after 1 h.

EXAMPLE 2

Sodium carbonate was added to an aqueous solution of Bronopol (10 µg/ml) to give a concentration of 0.1M $Na_2CO_3$. After 2 min, the solution was neutralized with an equivalent amount of acetic acid. Fast Red GG salt was added to give a concentration of 20 µg/ml. After 2 min, an amount of Na$_2$CO$_3$ similar to that used in the first step of the reaction was added, stabiliser (chlorinated phenol) was added, and the resulting red colour was measured after 5 min.

What is claimed is:

1. A method for assaying a compound or its derivatives formed by hydrolysis, in a sample, wherein the compound is selected from the group consisting of 2-bromo-2-nitro-1,3-propanediol, 2,2-dibromo-2-nitroethanol, which comprises adding to the sample a diazo compound which reacts with the compound or derivative formed by hydrolysis to be assayed to form a colored species, and determining the presence of the species colorimetrically.

2. A method according to claim 1, wherein the coloured species is red.

3. A method according to claim wherein the diazo compound is derived from 4-nitroaniline or another aniline having a 2- or 4-electron-withdrawing substituent.

4. A method according to claim 3, wherein the derivative formed by hydrolysis is 2-nitroethanol or 2-bromo-2-nitro-1,3-propanediol or a product of hydrolysis of the compound.

5. A method according to claim 1, wherein the colour forms in alkaline conditions.

6. A method according to claim 5, which comprises the steps of (1) making the sample alkaline; (2) neutralising the alkaline sample; (3) adding the diazo compound and making the neutral sample alkaline; and (4) determining the presence and, optionally the, concentration of the coloured species.

7. A method according to claim 6, which additionally comprises adding a stabiliser for the colour, between steps 3 and 4.

8. A method according to claim 1, which further comprises a prior step of removing from the sample substantially all components, other than the compound under test, which form coloured species by reaction with the diazo compound and/or under the assay conditions.

9. A method according to claim 1, wherein the compound under test is 2-bromo-2-nitro-1,3-propanediol.

10. The method of claim 1, further comprising determining the concentration of the species colorimetrically.

* * * * *